United States Patent [19]

Bergemann et al.

[11] Patent Number: 5,417,862

[45] Date of Patent: May 23, 1995

[54] PROCESS FOR INACTIVATING THE BIOLOGICAL ACTIVITY OF DNA

[75] Inventors: Klaus Bergemann, Biberach; Georg Bader, Birkenhard; Wolfgang Berthold; Rolf-Gunter Werner, both of Biberach, all of Germany

[73] Assignee: Dr. Karl Thomae Gesellschaft mit beschränkter Haftung, Germany

[21] Appl. No.: 942,057

[22] Filed: Sep. 8, 1992

Related U.S. Application Data

[63] Continuation of Ser. No. 701,147, May 17, 1991, abandoned.

[30] Foreign Application Priority Data

May 17, 1990 [DE] Germany ............ 40 15 832.2

[51] Int. Cl.6 ............ C02F 1/50; A61L 2/04; C12N 1/08
[52] U.S. Cl. ............ 210/626; 210/764; 210/766; 422/28
[58] Field of Search ............ 210/620, 626, 631, 749, 210/754, 759, 764–766; 422/28, 37; 424/605, 666

[56] References Cited

U.S. PATENT DOCUMENTS 3,227,626  1/1966  Baumgarten et al. ............ 195/66
5,120,452  6/1992  Ness et al. ............ 210/764

FOREIGN PATENT DOCUMENTS 1988888  7/1990  Australia .
0144714  6/1985  European Pat. Off. .
0278674  8/1988  European Pat. Off. .
2318225 11/1977  France .
13733921 4/1989  Germany .
1471336  4/1977  United Kingdom .
1498688  1/1978  United Kingdom .

OTHER PUBLICATIONS

Copy of European Search Report for corresponding European Application No. 91105898.0.

Primary Examiner—Thomas Wyse
Attorney, Agent, or Firm—Sterne, Kessler, Goldstein & Fox

[57] ABSTRACT

A process for inactivating the biological activity of DNA, especially recombinant DNA, is disclosed. The process includes the step of heating the DNA at 60° to 100° C. in the presence of an acid other than percarboxylic acid at a concentration of at least 0.2 mM and a pH value of maximum 4, preferably 3.

8 Claims, 2 Drawing Sheets

PROCESS FOR INACTIVATING THE BIOLOGICAL ACTIVITY OF DNA

This application is a continuation of application Ser. No. 07/701,147, filed May 17, 1991, abandoned.

FIELD OF THE INVENTION

This invention relates to a process for inactivating the biological activity of DNA, in particular recombinant DNA, and preferably the simultaneous killing of cells such as mammalian cells (e.g., CHO-, COS- and hybridoma cells), bacterial cells (e.g., *E. coli* and *B. subtilis*), or yeast. The present invention is particularly beneficial in pretreating a biomass influent stream to a waste treatment system. The pretreatment method is effective in inactivating the biological activity of DNA in the biomass influent stream.

BACKGROUND OF THE INVENTION

In work with recombinant DNA-containing microorganisms, waste material containing not only living organisms but also active nucleic acids are produced. This waste material must be inactivated in accordance with the respective safety requirements before the biomass can be passed to a purification plant.

Although many microorganisms and cell cultures can be killed by heating at 80° C., the DNA is not destroyed by such treatment. That is, vital cell functions such as respiration or photosynthesis may cease. However, nuclear material such as DNA or RNA may remain intact.

The known methods recognized by the Central Commission of Biological Safety (ZKBS) of the Federal Republic of Germany, for sterilization and cell inactivation (e.g. steam sterilization for 20 minutes at 121° C.) are very expensive. When used on an industrial scale, the recognized methods are cost intensive and may be impractical.

In these ZKBS-approved disposal processes, the DNA is degraded to units shorter than 500 base pairs. Units of this size are no longer biologically active and can be transferred into waste water without giving rise to any risks.

Generally, inactivation of cell biomass or cellular material must be carried out before being fed to the purification plant. Thus, it is of primary concern that substances used in inactivation procedures not be harmful or fatal to microorganisms. It is particularly important that such substances not be harmful to microorganisms commonly associated with the activated sludge purification process.

It is, moreover, desirable that the substance used is nontoxic or that it can be rendered harmless by being degraded by microorganisms such as bacteria present in an activated sludge process. It is also desirable that the inactivating substances have no negative influence on the walls and other surfaces of the fermentation and purification equipment. Preferably, such substances would have relatively minimal corrosive or erosive characteristics.

German Patent Application DE 05 37 33 921 describes a process for inactivating DNA, in particular recombinant DNA, wherein a percarboxylic acid with 1 to 3 carbon atoms or a salt thereof, an alkali peroxide or an alkali peroxomonosulfate is added to a DNA-containing biomass. The mixture is then heated at 60° to 100° C. for 20 to 60 minutes, preferably at pH 6 to 11. The percarboxylic acids, e.g. peroxyacetic acid, are, however, relatively unstable.

It is also known that a DNA chain when heated for 40 minutes at 100° C. in a phenol-containing saline solution is extensively degraded (Meth. Enzymol. B XII, page 97).

In another known process, Meth. Enzymol A XII, pages 222–223 describes the degradation of DNA to produce apurinic acid using 98% formic acid at 30° C. for 17 hours.

SUMMARY OF THE INVENTION

We have now surprisingly found that several storage stable, biologically degradable acids are capable of inactivating DNA and killing cells when used at certain pH values and concentrations. The process for achieving this inactivity is particularly beneficial in that it can be achieved at relatively low temperatures.

Accordingly, the present invention provides for a process for inactivating the biological activity of DNA comprising heating the DNA at a temperature of from about 60° to 100° C. in the presence of an acid other than percarboxylic acid at a concentration of at least 0.2 mM and a measurable pH of about 4. The present invention is particularly effective on an industrial scale when used to pretreat a waste treatment influent stream. Preferably, pretreatment is applied before the waste treatment stream is fed to an activated sludge unit.

BRIEF DESCRIPTION OF THE DRAWINGS

The present invention will be better understood by reference to the Description of the Preferred Embodiments when taken together with the attached drawings, wherein.

DESCRIPTION OF THE PREFERRED EMBODIMENTS

Figure 1:
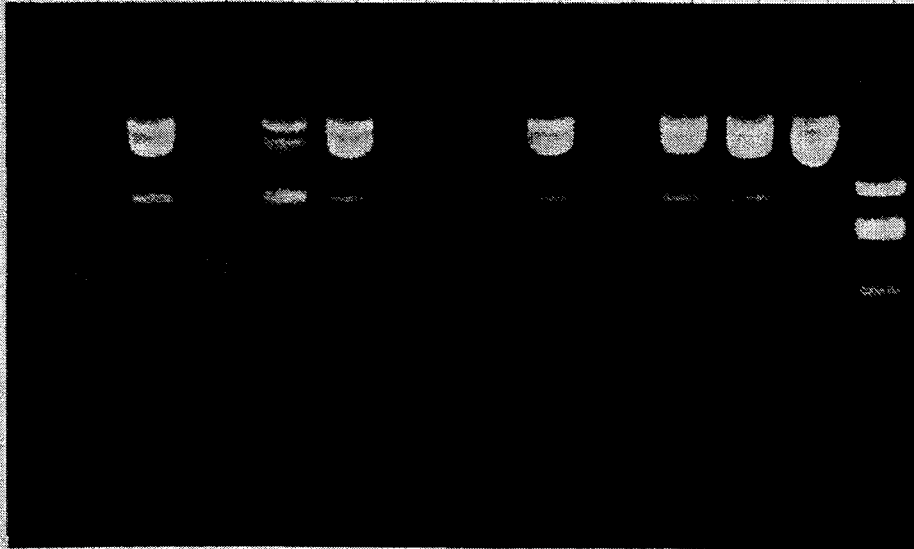
FIG. 1 shows the effects of the present invention on supercoiled DNA.

The subject of the invention is a process for inactivating the biological activity of DNA, particularly recombinant DNA. The process is characterized in that the DNA is heated at a temperature of from 60° to 100° C. in the presence of a biodegradable acid, excluding percarboxylic acids, at a concentration of at least 0.2 mM and a measurable pH of less than 4.

The terms "inactivating biological activity" or "inactivating cells" can be considered synonymous and can refer to the cessation of vital cell functions. Generally, this can refer to a substance which is capable of significantly inhibiting cell functions such as replication, transcription, and translation. The cessation of vital functions such as these are readily determinable by those of ordinary skill in the art. Typically, these functions can be monitored directly or indirectly by such methods as measuring respiration, elemental uptake, or photosynthesis.

The term "inactivating the biological activity of DNA" is considered to refer to the extent of degradation of DNA by the present invention. When DNA is cleaved such that it can no longer accomplish the roles of replication, transcription or translation, it is considered to be biologically inactivated. Preferably, the DNA will be cleaved into units which are shorter than 500 base pairs.

Although the preferred embodiment of the present invention results in inactivation of DNA, inactivation of any nucleic acid material can be achieved. This includes inactivation of RNA, recombinant nucleic acids such as recombinant DNA, or nucleic acid-protein conjugates such as ribozymes.

DNA is considered to be a "recombinant" if it results from the application of Recombinant DNA Techniques. Examples of recombinant DNA techniques include cloning, mutagenesis, transformation, etc. Recombinant DNA Techniques are disclosed in Maniatis, T., et al., *Molecular Cloning: A Laboratory Manual*, Cold Spring Harbor, N.Y. (1982).

The term "biodegradable acid" refers to any acid that can be degraded or decomposed by living organisms. It is preferred that such acid be able to be used as a carbon source for either gram negative or gram positive bacteria. In this way, the acid can be consumed by bacteria present in activated sludge. Given the particular type of bacteria which is present, one of ordinary skill can readily determine which acids can function as a carbon source. Such information is also available in references such as *Bergey's Manual of Determinative Bacteriology*.

The concentration of hydrogen ions in solution is a measure of the acidity or basicity of a solution. The pH value of a solution is a convenient way to express the concentration of hydrogen ions. The pH value is the negative power to which 10 must be raised to equal hydrogen ion concentration. For example, hydrochloric acid is completely ionized in dilute solution so the concentration of the hydrogen ion in a 0.01M HCl solution is $10^{-2}$M. Therefore, the pH of 0.01M HCl is 2. Using this standard method of determining pH, a measurable pH is considered to be a hydrogen ion concentration of greater than zero.

The process of this invention can be carried out as a biomass or isolated DNA. The biomass can be for example a culture medium containing a microorganism or a cell culture.

The present process can be carried out with acid at a concentration of 1 mM to 500 mM. Preferably, the process will be carried out at a concentration of 2 to 100 mM, with a concentration of 2.3 to 50 or 10 to 50 mM being most preferable.

The process according to the invention is normally carried out at a measurable pH of less than about 4. Preferably, the pH value will range between 1 and 3, with a pH range of 2 to 3 being most preferred.

Mammalian cells are preferably treated at a concentration of at least 100 mM and a maximum pH value of 3, most preferably at a pH of 2.5. In the case of bacteria, preferred treatment is at a concentration of at least 400 mM and a pH value of maximum 3.

As acids, organic acids such as formic acid, acetic acid, propionic acid, halogenated organic acids such as mono-, di-, trichloroacetic acid, oxalic acid, malonic acid, succinic acid, malic acid, citric acid, tartaric acid, lactic acid, maleic acid, fumaric acid, benzoic acid, salicylic acid, inorganic acids such as hydrochloric acid, bromic acid, fluoric acid, iodic acid, perchloric acid, sulfuric acid, sulfurous acid, nitric acid, nitrous acid, boric acid, phosphoric acid, and acid salts such as sodium hydrogen sulfate and sodium hydrogen sulfite as well as suitable combinations thereof, come into consideration. Preferably, citric acid, lactic acid, acetic acid, phosphoric acid or formic acid are used.

The heating of the mixture is carried out until no DNA with a chain length of more than 500 base pairs is electrophoretically detectable. As a rule this takes 10 to 70 minutes, preferably 20 to 60 minutes.

In order to check whether the entire DNA is degraded, aliquots are removed from the mixture and an Agarose-gel electrophoresis carried out. Cf. Harlow, E. et al., *Antibodies: A Laboratory Manual*, Cold Spring Harbor Laboratory (1988), and Sambrook et al., *Molecular Cloning: A Laboratory Manual*, 2d Ed., Cold Spring Harbor Laboratory (1989). The chromatographic separation is according to molecular weight and shows the fragments which are still present in the solution.

A particular advantage of the process is that not only normal double stranded DNA such as λ-DNA and genomic DNA from bacteria or mammalian cells can be inactivated, but "supercoiled-Plasmid DNA" can also be inactivated with certainty.

When the inactivation process of this invention is used as a pretreatment system, it is understood that subsequent to the inactivation of biological activity, the pH of the system can be neutralized. Before entering an activated sludge unit, it is common practice to neutralize an influent stream to achieve a pH range of between 6 and 8. This neutralization step is well known and is performed to ensure activity of the activated sludge.

Having now generally described this invention, the same will become more readily understood by reference to the following specific examples which are included herein for purposes of illustration only and are not intended to be limiting unless otherwise specified.

EXAMPLE 1

A sample containing 5 μg of DNA in aqueous solution (10μ) was placed in a 1.5 ml Eppendorf vessel. Acids in various preparations (10 μl) were added thereto and the resulting reaction mixture (end volume 20 μl) was incubated under the conditions set forth in the following Table 1. At the end of the incubation the mixture was neutralized by the addition of 5 μl 1M Tris pH 8.5.

10 μl of the DNA solution was removed after the acid treatment, mixed with 5 μl commercial buffer consisting of 20% Ficoll (Pharmacia Fine Chemicals), 0.050% bromophenol blue, 20 mM EDTA, and applied to an Agarose-electrophoresis plate (agarose concentration between 1 and 2%). The electrophoresis buffer consisted of 40 mM Tris acetate pH 7.8 and 1 mM EDTA. The electrophoresis was carried out at 30–50 Volt/cm.

The DNA length standards were λ-DNA digested with Bst EII or Hind III and plasmid-pBR 322 digested with Hinf I or Bst NI by which fragments with the following lengths were obtained:

λ-DNA/Hind III: 27491, 9416, 6557, 4361, 2322, 2027, 564, 125 pBR 322/Bst N1: 1857, 1060, 929, 383, 121, 13

The results are given in Table 1.

TABLE 1

| DNA or cells | Acid | Conc. | pH | Temp. | Incubation Period | Result |
|---|---|---|---|---|---|---|
| λ DNA 48,500 Bp Boehringer Mannheim | Citric acid | 3 mM | 3.1 | 70° C. | 10 to 30 Min. | Total breakdown to fragments <500 bp |
| λ DNA 48,500 Bp Boehringer Mannheim | Citric acid | 200 mM | 1.9 | 70° C. | 10 Min. | Total breakdown to fragments <500 bp |
| λ DNA 48,500 Bp Boehringer Mannheim | Citric acid | 10 mM | 2.8 | 70° C. | 60 Min. | Total breakdown to fragments <500 bp |
| λ DNA 48,500 Bp Boehringer Mannheim | Citric acid | 1 mM | 3.6 | 70° C. | 60 Min. | Total breakdown to fragments <500 bp |
| λ DNA 48,500 Bp Boehringer Mannheim | Citric acid | 2.3 mM | 3.1 | 60° C. | 60 Min. | Total breakdown to fragments <500 bp |
| CHO-cells (96% viable) | Citric acid | 50 mM | 2.3 | 70° C. | 60 Min. | Total breakdown to fragments <500 bp |
| CHO-cells (96% viable) | Citric acid | 100 mM | 2.1 | 70° C. | 60 Min. | Total breakdown to fragments <500 bp |
| CHO-cells (96% viable) | Citric acid | 200 mM | 1.9 | 70° C. | 60 Min. | Total breakdown to fragments <500 bp |
| CHO-cells (96% viable) | Citric acid | 500 mM | 1.7 | 70° C. | 60 Min. | Total breakdown to fragments <500 bp |
| E. coli HB 101 | Citric acid | 100 mM | 2.1 | 70° C. | 60 Min. | no viable cells[1] |
| E. coli HB 101 | Citric acid | 200 mM | 1.9 | 70° C. | 60 Min. | no viable cells[1] |
| E. coli HB 101 | Citric acid | 400 mM | 1.8 | 70° C. | 60 Min. | no viable cells and total breakdown of DNA to fragments <500 bp |
| E. coli HB 101 | Citric acid | 800 mM | 1.5 | 70° C. | 60 Min. | no viable cells and total breakdown of DNA to fragments <500 bp |
| E. coli HB 101 | Citric acid | 1000 mM | 1.4 | 70° C. | 60 Min. | no viable cells and total breakdown of DNA to fragments <500 bp |
| Plasmid DNA (pBR 322) (supercoiled 4,300 bp) | Formic acid | 10 mM | 3.6 | 70° C. | 60 Min. | Total breakdown to fragments <500 bp |
| Plasmid DNA (pBR 322) (supercoiled 4,300 bp) | Formic acid | 1 mM | 4.0 | 70° C. | 60 Min. | Total breakdown to fragments <500 bp |
| Plasmid DNA (pBR 322) (supercoiled 4,300 bp) | $H_3PO_4$ | 3 mM | 2.9 | 70° C. | 60 Min. | Total breakdown to fragments <500 bp |
| Plasmid DNA (pBR 322) (supercoiled 4,300 bp) | $H_3PO_4$ | 0.3 mM | 3.8 | 70° C. | 60 Min. | Total breakdown to fragments <500 bp |
| Plasmid DNA (pBR 322) (supercoiled 4,300 bp) | HCl | 10 mM | 2.3 | 70° C. | 60 Min. | Total breakdown to fragments <500 bp |
| Plasmid DNA (pBR 322) (supercoiled 4,300 bp) | HCl | 1 mM | 3.3 | 70° C. | 60 Min. | Total breakdown to fragments <500 bp |
| Plasmid DNA (pBR 322) (supercoiled 4,300 bp) | Citric acid | 2.3 mM | 3.1 | 60° C. | 60 Min. | Total breakdown to fragments <500 bp |

[1]By cultivation on Agar plates and in liquid culture for over 7 days at 37° C.

EXAMPLE 2

Example 1 was repeated by using pBR 322 (supercoiled DNA) with various concentrations of acid as indicated in Table 2.

The reaction mixture was incubated for 60 minutes at 70° C.

TABLE 2

| Lane | | | pH |
|---|---|---|---|
| 1 | Citric acid | 10 mM | 2.8 |
| 2 | Citric acid | 1 mM | 3.6 |
| 3 | Citric acid | 0.1 mM | 4.3 |
| 4 | Acetic acid | 10 mM | 3.6 |
| 5 | Acetic acid | 1 mM | 4.1 |
| 6 | Acetic acid | 0.1 mM | 4.4 |
| 7 | Hydrochloric acid | 10 mM | 2.3 |
| 8 | Hydrochloric acid | 1 mM | 3.3 |
| 9 | Hydrochloric acid | 0.1 mM | 4.1 |
| 10 | Phosphoric acid | 3 mM | 2.4 |
| 11 | Phosphoric acid | 0.3 mM | 3.1 |
| 12 | Phosphoric acid | 0.03 mM | 4.0 |
| 13 | no acid | | |
| 14 | Length standards pBR 322/ | | |

TABLE 2-continued

| Lane | pH |
|---|---|
| Bst N1 | |

FIG. 1 shows the electrophoresis results of such a test. It shows clearly that the incubation of the DNA in accordance with the invention (Lanes 1, 2, 4, 5, 7, 8 and 10) results in a breakdown to fragments smaller than 300 bp. The control, lane 13, shows no breakdown into smaller fragments.

EXAMPLE 3

Example 1 was repeated but using Lambda-Phage DNA with various acids of different concentrations as shown in Table 3.

The reaction mixture was incubated for 60 minutes at 70° C.

TABLE 3

| Lane | | | pH |
|---|---|---|---|
| 1 | Citric acid | 10 mM | 2.8 |
| 2 | Citric acid | 1 mM | 3.6 |
| 3 | Citric acid | 0.1 mM | 4.3 |
| 4 | Acetic acid | 10 mM | 3.6 |
| 5 | Acetic acid | 1 mM | 4.1 |
| 6 | Acetic acid | 0.1 mM | 4.4 |
| 7 | Hydrochloric acid | 10 mM | 2.3 |
| 8 | Hydrochloric acid | 1 mM | 3.3 |
| 9 | Hydrochloric acid | 0.1 mM | 4.1 |
| 10 | Phosphoric acid | 3 mM | 2.4 |
| 11 | Phosphoric acid | 0.3 mM | 3.1 |
| 12 | Phosphoric acid | 0.03 mM | 4.0 |
| 13 | no acid | | |
| 14 | Length standards pBR 322/ Bst N1 | | |

Figure 2:
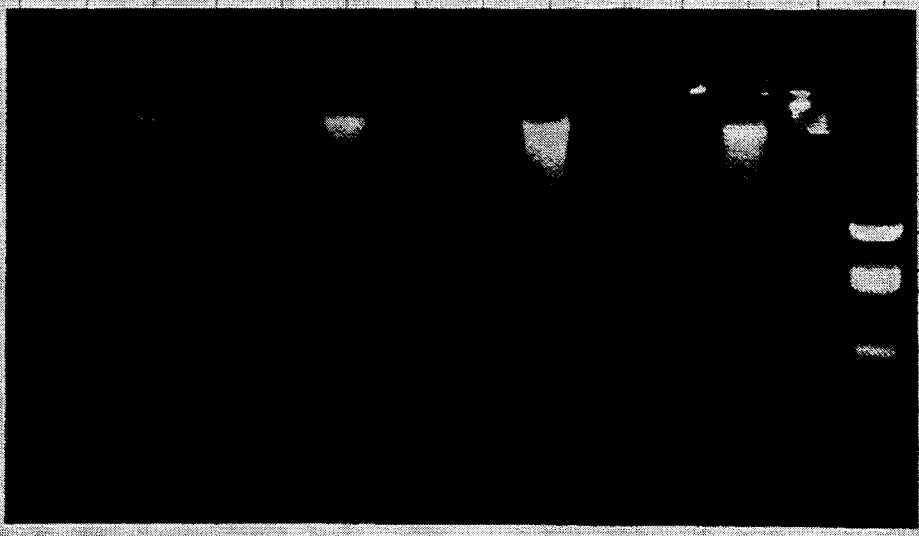
FIG. 2 shows the effects of the present invention on Lambda-Phage DNA.

The results are shown in FIG. 2. This figure shows that by treatment of the Lambda-phage DNA according to the invention (Lanes 1, 2, 4, 5, 7, 8, 10 and 11) fragmentation of the DNA is detectable. The control, lane 13, shows no breakdown into smaller fragments.

EXAMPLE 4

Treatment of recombinant CHO-cells with acid

Aliquots containing $1 \times 10^7$ cells were removed from a suspension culture of recombinant CHO-cells ($3 \times 10^6$ cells/ml; viability 96%), and citric acid added thereto. The end volume was 1 ml. The concentration of the citric acid was: [mM] 400, 200, 100, 50, 20, 10. A sample was mixed with water as a control. An incubation followed at 70° C. for 60 minutes (see Table 4).

Finally, the reaction mixture, after the addition of 1M Tris pH 8.5 to bring the pH value to 7, was incubated for 60 minutes with Proteinase K (final concentration: 0.4 mg/ml) and extracted twice with phenol/choroform (1:1). The aqueous residue was desalted over a Sephadex-G25 column, concentrated 90-fold and 10 μl thereof, corresponding to 200 μl of the suspension culture, investigated using the Agarose-gelelectrophoresis (1.8% Agarose).

Figure 3:
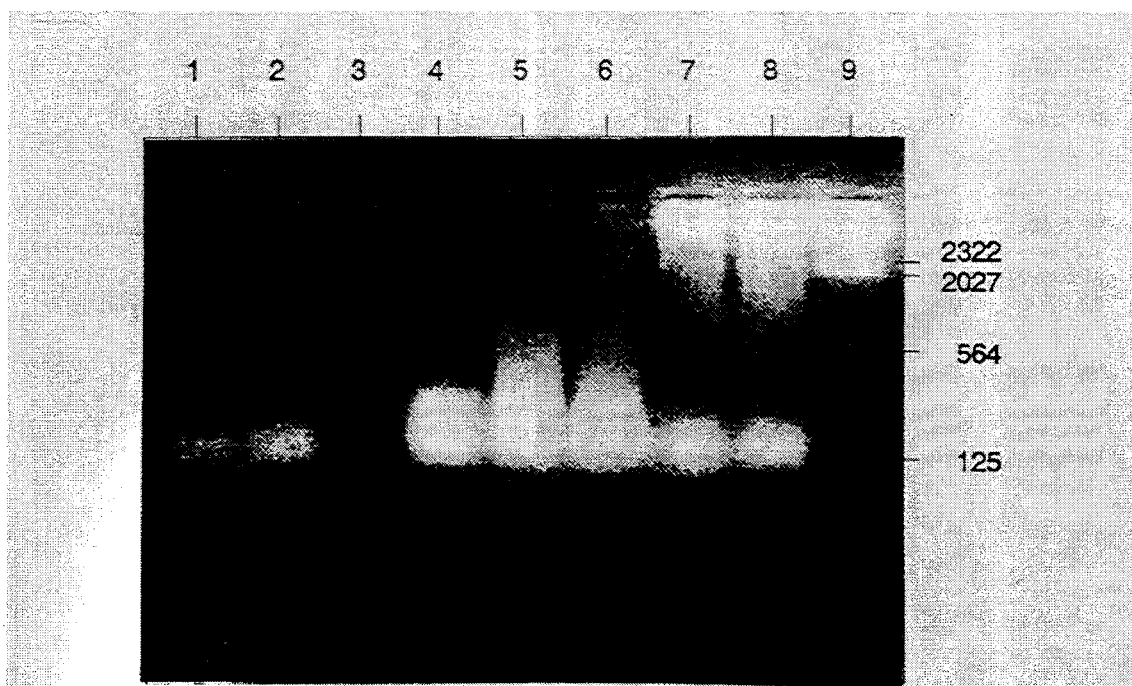
FIG. 3 shows the effects of the present invention on CHO-cells.

The results are given in FIG. 3. This figure shows that upon the treatment of viable CHO-cells according to the invention (Lanes 1 to 6) a strong denaturing and the breakdown of the DNA to fragments with approximately 125 base pairs (Lanes 1 to 4) is detectable. Controls 7 and 8 show DNA at the uncleaved region as well as at the 125 base pair region.

TABLE 4

| Lane | | | | pH of entire solution |
|---|---|---|---|---|
| 1 | CHO-cells | 400 mM Citric acid | 70° C./60 Min. | 2.1 |
| 2 | CHO-cells | 200 mM Citric acid | 70° C./60 Min. | 2.3 |
| 3 | CHO-cells | 100 mM Citric acid | 70° C./60 Min. | 2.6 |
| 4 | CHO-cells | 50 mM Citric acid | 70° C./60 Min. | 3.0 |
| 5 | CHO-cells | 20 mM Citric acid | 70° C./60 Min. | 3.7 |
| 6 | CHO-cells | 10 mM Citric acid | 70° C./60 Min. | 4.2 |
| 7 | CHO-cells | without Citric acid | 70° C./60 Min. | 6.6 |
| 8 | CHO-cells | untreated cells | | |
| 9 | Length standard Lambda DNA/ Hind III | | | |

EXAMPLE 5

Treatment of *E. Coli* (Strain HB 101) and *Bacillus subtilis* (ATCC 6633)

1 ml portions of a bacteria culture was mixed with respective 1 ml portions of citric acid of increasing concentration, such that the following end concentrations were obtained: 0.2M; 0.4M; 0.8M; 1.0M. 1 ml water in place of citric acid was added to one sample as a control (see Table 5).

All samples were incubated at 70° for one hour. The sample is finally centrifuged for 5 minutes at 12,000 xg and the sediment digested with proteinase K (final concentration 100 μ/ml) for 1 hour at 37° C. in order to open the cell membrane and free the bound DNA.

In order to separate the membrane parts, which would disturb the further analysis, sodium chloride (final concentration: 0.7M) and cetyl-trimethyl-ammonium bromide (Serva, Heidelberg, Order No. 16530) (final concentration: 1%) was added to the sample which was then incubated at 65° C. for 10 minutes and finally extracted with 1/1 volume chloroform-/isoamylalcohol (24:1). The aqueous phase, containing DNA, was purified by extraction with phenol/-chloroform/isoamylalcohol (25:24:1) and the aqueous residue investigated by means of agarose electrophoresis. The electrophoresis was carried out using 10 μl of the purified DNA solution corresponding to 0.4 ml of the culture broth.

Figure 4:
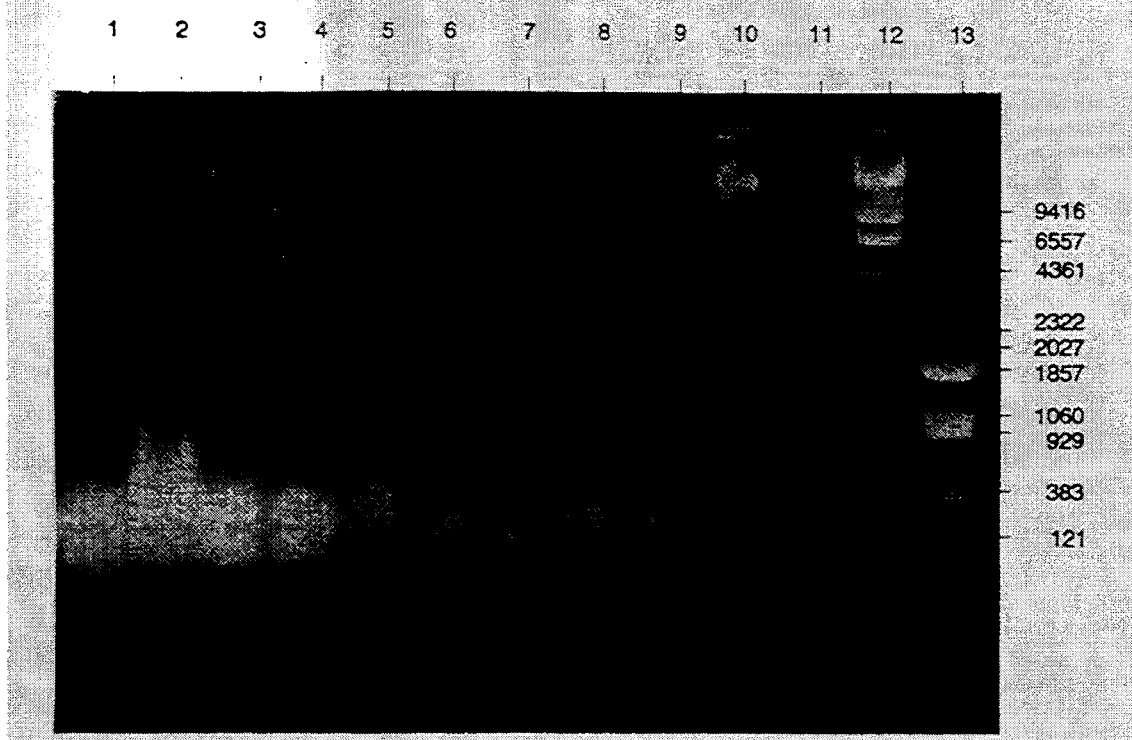
FIG. 4 shows the effects of the present invention on a bacterial culture of *Escherichia coli* and *Bacillus subtilis*.

The results are shown in the Electropherogram of FIG. 4. This figure shows that after the treatment of the bacteria according to the invention, only DNA-fragments of approximately 100 bp are detectable.

TABLE 5

| Lane | | | pH |
|---|---|---|---|
| 1 | E. coli | 0.2 M Citric acid | 1.9 |
| 2 | E. coli | 0.4 M Citric acid | 1.8 |
| 3 | E. coli | 0.8 M Citric acid | 1.5 |
| 4 | E. coli | 1.0 M Citric acid | 1.4 |
| 5 | E. coli | without Citric acid | |
| 6 | B. subtilis | 0.2 M Citric acid | 1.9 |
| 7 | B. subtilis | 0.4 M Citric acid | 1.8 |
| 8 | B. subtilis | 0.8 M Citric acid | 1.5 |
| 9 | B. subtilis | 1.0 M Citric acid | 1.4 |
| 10 | B. subtilis | without Citric acid | |
| 11 | empty | | |
| 12 | Length standard Lambda DNA/ Hind III | | |
| 13 | Length standard pBR 322/Bst N1 | | |

Having now fully described this invention, it will be appreciated by those skilled in the art that the same can be performed within a wide range of equivalent parameters of composition, concentrations, modes of administration, and conditions without departing from the spirit or scope of the invention or of any embodiment thereof.

What is claimed is:

1. A process for inactivating the biological activity of DNA comprising heating the DNA at a temperature of from about 60° to 100° C. in the presence of an acid other than a percarboxylic acid at a concentration of at least 0.2 mM and a measurable pH of less than about 4.

2. The process of claim 1, wherein the acid is biologically degradable.

3. The process of claim 1, wherein the acid is citric acid, lactic acid, acetic acid, phosphoric acid, or formic acid.

4. The process of any one of claims 1, 2 or 3, wherein the process further biologically inactivates cells selected from the group consisting of CHO, *E. coli* and *Bacillus subtilis*.

5. The process of claim 1, wherein the DNA is inactivated as a pretreatment step in an activated sludge treatment system.

6. The process of claim 1, wherein the process is applied to a waste treatment influent stream.

7. The process of claim 6, wherein the influent stream is treated before contact with activated sludge.

8. The process of claim 1, wherein the pH is between 1 and 3.

* * * * *